(12) United States Patent
Nageri et al.

(10) Patent No.: US 10,905,871 B2
(45) Date of Patent: Feb. 2, 2021

(54) LEAD ASSEMBLIES WITH ARRANGEMENTS TO CONFIRM ALIGNMENT BETWEEN TERMINALS AND CONTACTS

(71) Applicant: Boston Scientific Neuromodulation Corporation, Valencia, CA (US)

(72) Inventors: Ranjan Krishna Mukhari Nageri, Valencia, CA (US); Peter J. Yoo, Burbank, CA (US)

(73) Assignee: BOSTON SCIENTIFIC NEUROMODULATION CORPORATION, Valencia, CA (US)

(*) Notice: Subject to any disclaimer, the term of this patent is extended or adjusted under 35 U.S.C. 154(b) by 386 days.

(21) Appl. No.: 15/878,085

(22) Filed: Jan. 23, 2018

(65) Prior Publication Data
US 2018/0214687 A1    Aug. 2, 2018

Related U.S. Application Data

(60) Provisional application No. 62/451,513, filed on Jan. 27, 2017.

(51) Int. Cl.
*A61N 1/05*    (2006.01)
*H01R 13/641*    (2006.01)
(Continued)

(52) U.S. Cl.
CPC ......... *A61N 1/0553* (2013.01); *H01R 13/641* (2013.01); *H01R 24/58* (2013.01);
(Continued)

(58) Field of Classification Search
CPC combination set(s) only.
See application file for complete search history.

(56) References Cited

U.S. PATENT DOCUMENTS 3,222,471 A    12/1965    Steinkamp
3,601,747 A    8/1971    Prat et al.
(Continued)

FOREIGN PATENT DOCUMENTS

EP    0580928 A1    2/1994
EP    0650694 B1    7/1998
(Continued)

*Primary Examiner* — Joseph M Dietrich
(74) *Attorney, Agent, or Firm* — Branch Partners PLLC; Bruce E. Black

(57) ABSTRACT

A lead assembly includes a lead or lead extension having terminals and a mechanical stop fixed to the lead or lead extension and located distally to the plurality of terminals. The lead assembly also includes a connector having a connector housing, a connector block disposed within the connector housing, a port defined at the distal surface of the connector housing, a lumen extending from the port for receiving a portion the lead or lead extension, and contacts disposed within the connector housing. The outer diameter of the mechanical stop is larger than the lumen diameter within the connector block to halt further insertion of the lead or lead extension into the connector housing. Additionally or alternatively, a visually distinctive marking can be applied to the lead or lead extension to indicate alignment between the terminals of the lead and the contacts of the connector.

14 Claims, 8 Drawing Sheets

(51) Int. Cl.
*H01R 24/58* (2011.01)
*A61N 1/375* (2006.01)
*H01R 107/00* (2006.01)

(52) U.S. Cl.
CPC ........ *A61N 1/3752* (2013.01); *H01R 2107/00* (2013.01); *H01R 2201/12* (2013.01)

(56) References Cited

U.S. PATENT DOCUMENTS

| | | |
|---|---|---|
| 3,718,142 A | 2/1973 | Mulier |
| 3,757,789 A | 9/1973 | Shanker |
| 3,771,106 A | 11/1973 | Matsumoto et al. |
| 3,908,668 A | 9/1975 | Bolduc |
| 3,951,154 A | 4/1976 | Hartlaub |
| 3,990,727 A | 11/1976 | Gallagher |
| 4,003,616 A | 1/1977 | Springer |
| 4,112,953 A | 9/1978 | Shanker et al. |
| 4,142,532 A | 3/1979 | Ware |
| 4,180,078 A | 12/1979 | Anderson |
| 4,245,642 A | 1/1981 | Skubitz et al. |
| 4,259,962 A | 4/1981 | Peers-Trevarton |
| 4,310,001 A | 1/1982 | Comben |
| 4,364,625 A | 12/1982 | Baker et al. |
| 4,367,907 A | 1/1983 | Buck |
| 4,411,276 A | 10/1983 | Dickhudt et al. |
| 4,411,277 A | 10/1983 | Dickhudt |
| 4,461,194 A | 7/1984 | Moore |
| 4,466,441 A | 8/1984 | Skubitz et al. |
| 4,516,820 A | 5/1985 | Kuzma |
| RE31,990 E | 9/1985 | Sluetz et al. |
| 4,540,236 A | 9/1985 | Peers-Trevarton |
| 4,602,624 A | 7/1986 | Naples et al. |
| 4,603,696 A | 8/1986 | Cross, Jr. et al. |
| 4,614,395 A | 9/1986 | Peers-Trevarton |
| 4,630,611 A | 12/1986 | King |
| 4,695,116 A | 9/1987 | Bailey et al. |
| 4,695,117 A | 9/1987 | Kysiak |
| 4,712,557 A | 12/1987 | Harris |
| 4,715,380 A | 12/1987 | Harris |
| 4,744,370 A | 5/1988 | Harris |
| 4,784,141 A | 11/1988 | Peers-Trevarton |
| 4,832,032 A | 5/1989 | Schneider |
| 4,840,580 A | 6/1989 | Saell et al. |
| 4,850,359 A | 7/1989 | Putz |
| 4,860,750 A | 8/1989 | Frey et al. |
| 4,867,708 A | 9/1989 | Iizuka |
| 4,869,255 A | 9/1989 | Putz |
| 4,898,173 A | 2/1990 | Daglow et al. |
| 4,899,753 A | 2/1990 | Inoue et al. |
| 4,951,687 A | 8/1990 | Ufford et al. |
| 4,995,389 A | 2/1991 | Harris |
| 5,000,177 A | 3/1991 | Hoffmann et al. |
| 5,000,194 A | 3/1991 | van den Honert et al. |
| 5,007,435 A | 4/1991 | Doan et al. |
| 5,007,864 A | 4/1991 | Stutz, Jr. |
| 5,070,605 A | 12/1991 | Daglow et al. |
| 5,082,453 A | 1/1992 | Stutz, Jr. |
| 5,086,773 A | 2/1992 | Ware |
| 5,135,001 A | 8/1992 | Sinofsky et al. |
| 5,193,539 A | 3/1993 | Schulman et al. |
| 5,193,540 A | 3/1993 | Schulman et al. |
| 5,201,865 A | 4/1993 | Kuehn |
| 5,241,957 A | 9/1993 | Camps et al. |
| 5,252,090 A | 10/1993 | Giurtino et al. |
| 5,261,395 A | 11/1993 | Oleen et al. |
| 5,312,439 A | 5/1994 | Loeb |
| 5,324,312 A | 6/1994 | Stokes et al. |
| 5,330,521 A | 7/1994 | Cohen |
| 5,336,246 A | 8/1994 | Dantanarayana |
| 5,348,481 A | 9/1994 | Ortiz |
| 5,354,326 A | 10/1994 | Comben et al. |
| 5,358,514 A | 10/1994 | Schulman et al. |
| 5,368,496 A | 11/1994 | Ranalletta et al. |
| 5,374,279 A | 12/1994 | Duffin, Jr. et al. |
| 5,374,285 A | 12/1994 | Vaiani et al. |
| 5,383,913 A | 1/1995 | Schiff |
| 5,413,595 A | 5/1995 | Stutz, Jr. |
| 5,433,734 A | 7/1995 | Stokes et al. |
| 5,435,731 A | 7/1995 | Kang |
| 5,458,629 A | 10/1995 | Baudino et al. |
| 5,486,202 A | 1/1996 | Bradshaw |
| 5,489,225 A | 2/1996 | Julian |
| 5,509,928 A | 4/1996 | Acken |
| 5,522,874 A | 6/1996 | Gates |
| 5,534,019 A | 7/1996 | Paspa |
| 5,545,188 A | 8/1996 | Bradshaw et al. |
| 5,545,189 A | 8/1996 | Fayram |
| 5,560,358 A | 10/1996 | Arnold et al. |
| 5,582,180 A | 12/1996 | Manset et al. |
| 5,679,026 A | 10/1997 | Fain et al. |
| 5,683,433 A | 11/1997 | Carson |
| 5,711,316 A | 1/1998 | Elsberry et al. |
| 5,713,922 A | 2/1998 | King |
| 5,720,631 A | 2/1998 | Carson et al. |
| 5,730,628 A | 3/1998 | Hawkins |
| 5,755,743 A | 5/1998 | Volz et al. |
| 5,766,042 A | 6/1998 | Ries et al. |
| 5,782,892 A | 7/1998 | Castle et al. |
| 5,796,044 A | 8/1998 | Cobian et al. |
| 5,800,350 A | 9/1998 | Coppleson et al. |
| 5,800,495 A | 9/1998 | Machek et al. |
| 5,807,144 A | 9/1998 | Sivard |
| 5,837,006 A | 11/1998 | Ocel et al. |
| 5,843,141 A | 12/1998 | Bischoff et al. |
| 5,843,148 A | 12/1998 | Gijsbers et al. |
| 5,906,634 A | 5/1999 | Flynn et al. |
| 5,931,861 A | 8/1999 | Werner et al. |
| 5,938,688 A | 8/1999 | Schiff |
| 5,951,595 A | 9/1999 | Moberg et al. |
| 5,968,082 A | 10/1999 | Heil |
| 5,987,361 A | 11/1999 | Mortimer |
| 5,989,077 A | 11/1999 | Mast et al. |
| 6,006,135 A | 12/1999 | Kest et al. |
| 6,018,684 A | 1/2000 | Bartig et al. |
| 6,038,479 A | 3/2000 | Werner et al. |
| 6,038,481 A | 3/2000 | Werner et al. |
| 6,042,432 A | 3/2000 | Hashazawa et al. |
| 6,051,017 A | 4/2000 | Loeb et al. |
| 6,080,188 A | 6/2000 | Rowley et al. |
| 6,112,120 A | 8/2000 | Correas |
| 6,112,121 A | 8/2000 | Paul et al. |
| 6,125,302 A | 9/2000 | Kuzma |
| 6,134,478 A | 10/2000 | Spehr |
| 6,154,678 A | 11/2000 | Laura |
| 6,161,047 A | 12/2000 | King et al. |
| 6,162,101 A | 12/2000 | Fischer et al. |
| 6,164,284 A | 12/2000 | Schulman et al. |
| 6,167,311 A | 12/2000 | Rezai |
| 6,167,314 A | 12/2000 | Fischer, Sr. et al. |
| 6,175,710 B1 | 1/2001 | Kamaji et al. |
| 6,181,969 B1 | 1/2001 | Gord |
| 6,185,452 B1 | 2/2001 | Schulman et al. |
| 6,192,278 B1 | 2/2001 | Werner et al. |
| 6,198,969 B1 | 3/2001 | Kuzma |
| 6,208,894 B1 | 3/2001 | Schulman et al. |
| 6,224,450 B1 | 5/2001 | Norton |
| 6,271,094 B1 | 8/2001 | Boyd et al. |
| 6,295,944 B1 | 10/2001 | Lovett |
| 6,319,021 B1 | 11/2001 | Billman |
| 6,321,126 B1 | 11/2001 | Kuzma |
| 6,322,559 B1 | 11/2001 | Daulton et al. |
| 6,343,233 B1 | 1/2002 | Werner et al. |
| 6,364,278 B1 | 4/2002 | Lin et al. |
| 6,370,434 B1 | 4/2002 | Zhang et al. |
| 6,391,985 B1 | 5/2002 | Goode et al. |
| 6,397,108 B1 | 5/2002 | Camps et al. |
| 6,415,168 B1 | 7/2002 | Putz |
| 6,428,336 B1 | 8/2002 | Akerfeldt |
| 6,428,368 B1 | 8/2002 | Hawkins et al. |
| 6,430,442 B1 | 8/2002 | Peters et al. |
| 6,466,824 B1 | 10/2002 | Struble |
| 6,473,654 B1 | 10/2002 | Chinn |
| 6,498,952 B2 | 12/2002 | Imani et al. |
| 6,510,347 B2 | 1/2003 | Borkan |

(56) References Cited

U.S. PATENT DOCUMENTS

| | | |
|---|---|---|
| 6,516,227 B1 | 2/2003 | Meadows et al. |
| 6,556,873 B1 | 4/2003 | Smits |
| 6,564,078 B1 | 5/2003 | Marino et al. |
| 6,604,283 B1 | 8/2003 | Kuzma |
| 6,605,094 B1 | 8/2003 | Mann et al. |
| 6,609,029 B1 | 8/2003 | Mann et al. |
| 6,609,032 B1 | 8/2003 | Woods et al. |
| 6,654,641 B1 | 11/2003 | Froberg |
| 6,662,035 B2 | 12/2003 | Sochor |
| 6,663,570 B2 | 12/2003 | Mott |
| 6,671,534 B2 | 12/2003 | Putz |
| 6,671,553 B1 | 12/2003 | Helland et al. |
| 6,678,564 B2 | 1/2004 | Ketterl et al. |
| 6,725,096 B2 | 4/2004 | Chinn et al. |
| 6,741,892 B1 | 5/2004 | Meadows et al. |
| 6,757,039 B2 | 6/2004 | Ma |
| 6,757,970 B1 | 7/2004 | Kuzma et al. |
| 6,799,991 B2 | 10/2004 | Williams et al. |
| 6,805,675 B1 | 10/2004 | Gardeski et al. |
| 6,854,994 B2 | 2/2005 | Stein et al. |
| 6,878,013 B1 | 4/2005 | Behan |
| 6,895,276 B2 | 5/2005 | Kast et al. |
| 6,913,478 B2 | 7/2005 | Lamrey |
| 6,921,295 B2 | 7/2005 | Sommer et al. |
| 6,968,235 B2 | 11/2005 | Belden et al. |
| 6,980,863 B2 | 12/2005 | van Venrooij et al. |
| 7,027,852 B2 | 4/2006 | Helland |
| 7,047,084 B2 | 5/2006 | Erickson et al. |
| 7,058,452 B2 | 6/2006 | Dahberg |
| 7,069,081 B2 | 6/2006 | Biggs et al. |
| 7,083,474 B1 | 8/2006 | Fleck et al. |
| 7,108,549 B2 | 9/2006 | Lyu et al. |
| 7,110,827 B2 | 9/2006 | Sage et al. |
| 7,128,600 B2 | 10/2006 | Osypka |
| 7,155,283 B2 | 12/2006 | Ries et al. |
| 7,164,951 B2 | 1/2007 | Ries et al. |
| 7,168,165 B2 | 1/2007 | Calzada et al. |
| 7,191,009 B2 | 3/2007 | Laske et al. |
| 7,195,523 B2 | 3/2007 | Naviaux |
| 7,203,548 B2 | 4/2007 | Whitehurst et al. |
| 7,225,034 B2 | 5/2007 | Ries et al. |
| 7,231,253 B2 | 6/2007 | Tidemand et al. |
| 7,241,180 B1 | 7/2007 | Rentas |
| 7,242,987 B2 | 7/2007 | Holleman et al. |
| 7,244,150 B1 | 7/2007 | Brase et al. |
| 7,270,568 B2 | 9/2007 | Osypka |
| 7,283,878 B2 | 10/2007 | Brostrom et al. |
| 7,286,882 B2 | 10/2007 | Cole |
| 7,287,995 B2 | 10/2007 | Stein et al. |
| 7,292,890 B2 | 11/2007 | Whitehurst et al. |
| 7,396,335 B2 | 7/2008 | Gardeski et al. |
| 7,402,083 B2 | 7/2008 | Kast et al. |
| 7,422,487 B2 | 9/2008 | Osypka |
| 7,430,958 B2 | 10/2008 | Wong |
| 7,437,193 B2 | 10/2008 | Parramon et al. |
| 7,450,997 B1 | 11/2008 | Pianca et al. |
| 7,489,971 B1 | 2/2009 | Franz |
| 7,512,446 B2 | 3/2009 | Honeck |
| 7,516,447 B2 | 4/2009 | Marvin et al. |
| 7,526,339 B2 | 4/2009 | Lahti et al. |
| 7,539,542 B1 | 5/2009 | Malinowski |
| 7,548,788 B2 | 6/2009 | Chinn et al. |
| 7,554,493 B1 | 6/2009 | Rahman |
| 7,583,999 B2 | 9/2009 | Bedenbaugh |
| 7,585,190 B2 | 9/2009 | Osypka |
| 7,590,451 B2 | 9/2009 | Tronnes et al. |
| 7,650,184 B2 | 1/2010 | Walter |
| 7,668,601 B2 | 2/2010 | Hegland et al. |
| 7,672,734 B2 | 3/2010 | Anderson et al. |
| 7,736,191 B1 | 6/2010 | Sochor |
| 7,758,384 B2 | 7/2010 | Alexander et al. |
| 7,761,165 B1 | 7/2010 | He et al. |
| 7,761,985 B2 | 7/2010 | Hegland et al. |
| 7,783,359 B2 | 8/2010 | Meadows |
| 7,792,590 B1 | 9/2010 | Pianca et al. |
| 7,798,864 B2 | 9/2010 | Barker et al. |
| 7,803,021 B1 | 9/2010 | Brase |
| 7,809,446 B2 | 10/2010 | Meadows |
| 7,822,477 B2 | 10/2010 | Rey et al. |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,949,395 B2 | 5/2011 | Kuzma |
| 7,974,705 B2 | 7/2011 | Zdeblick et al. |
| 7,974,706 B2 | 7/2011 | Moffitt et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,046,073 B1 | 10/2011 | Pianca |
| 8,046,074 B2 | 10/2011 | Barker |
| 8,078,280 B2 | 12/2011 | Sage |
| 8,099,177 B2 | 1/2012 | Dahlberg |
| 8,100,726 B2 | 1/2012 | Harlan et al. |
| 8,140,163 B1 | 3/2012 | Daglow et al. |
| 8,167,660 B2 | 5/2012 | Dilmaghanian et al. |
| 8,175,710 B2 | 5/2012 | He |
| 8,190,259 B1 | 5/2012 | Smith et al. |
| 8,206,180 B1 | 6/2012 | Kast et al. |
| 8,224,450 B2 | 7/2012 | Brase |
| 8,225,504 B2 | 7/2012 | Dye et al. |
| 8,239,042 B2 | 8/2012 | Chinn et al. |
| 8,271,094 B1 | 9/2012 | Moffitt et al. |
| 8,295,944 B2 | 10/2012 | Howard et al. |
| 8,301,255 B2 | 10/2012 | Barker |
| 8,321,025 B2 | 11/2012 | Bedenbaugh |
| 8,342,887 B2 | 1/2013 | Gleason et al. |
| 8,359,107 B2 | 1/2013 | Pianca et al. |
| 8,364,278 B2 | 1/2013 | Pianca et al. |
| 8,391,985 B2 | 3/2013 | McDonald |
| 8,412,330 B2 | 4/2013 | Kast et al. |
| 8,527,054 B2 | 9/2013 | North |
| 8,583,237 B2 | 11/2013 | Bedenbaugh |
| 8,600,507 B2 | 12/2013 | Brase et al. |
| 8,682,439 B2 | 3/2014 | DeRohan et al. |
| 8,688,235 B1 | 4/2014 | Pianca |
| 8,784,143 B2 | 7/2014 | Edgell et al. |
| 8,831,742 B2 | 9/2014 | Pianca et al. |
| 8,849,396 B2 | 9/2014 | DeRohan et al. |
| 8,849,415 B2 | 9/2014 | Bedenbaugh |
| 8,897,876 B2 | 11/2014 | Sundaramurthy et al. |
| 8,897,891 B2 | 11/2014 | Romero |
| 8,968,331 B1 | 3/2015 | Sochor |
| 9,101,775 B2 | 8/2015 | Barker |
| 9,149,630 B2 | 10/2015 | Howard et al. |
| 9,162,048 B2 | 10/2015 | Romero et al. |
| 9,234,591 B2 | 1/2016 | Dilmaghanian et al. |
| 9,270,070 B2 | 2/2016 | Pianca |
| 9,289,596 B2 | 3/2016 | Leven |
| 9,352,147 B2 | 5/2016 | Nguyen-stella et al. |
| 9,381,348 B2 | 7/2016 | Romero et al. |
| 9,403,022 B2 | 8/2016 | Ries et al. |
| 9,409,032 B2 | 8/2016 | Brase et al. |
| 9,440,066 B2 | 9/2016 | Black |
| 9,498,618 B2 | 11/2016 | Stetson et al. |
| 9,498,620 B2 | 11/2016 | Romero et al. |
| 9,504,839 B2 | 11/2016 | Leven |
| 9,604,068 B2 | 3/2017 | Malinowski |
| 9,656,093 B2 | 5/2017 | Villarta et al. |
| 9,770,598 B2 | 9/2017 | Malinowski et al. |
| 9,855,413 B2 | 1/2018 | Vadlamudi et al. |
| 2001/0023368 A1 | 9/2001 | Black et al. |
| 2002/0143376 A1 | 10/2002 | Chinn et al. |
| 2002/0156513 A1 | 10/2002 | Borkan |
| 2002/0183817 A1 | 12/2002 | Van Venrooij et al. |
| 2003/0163171 A1 | 8/2003 | Kast et al. |
| 2004/0064164 A1 | 4/2004 | Ries et al. |
| 2004/0230268 A1 | 11/2004 | Huff et al. |
| 2004/0260373 A1 | 12/2004 | Ries et al. |
| 2005/0015130 A1 | 1/2005 | Gill |
| 2005/0027326 A1 | 2/2005 | Ries et al. |

(56) References Cited

U.S. PATENT DOCUMENTS

| | | |
|---|---|---|
| 2005/0027327 A1 | 2/2005 | Ries et al. |
| 2005/0038489 A1 | 2/2005 | Grill |
| 2005/0043770 A1 | 2/2005 | Hine et al. |
| 2005/0043771 A1* | 2/2005 | Sommer .............. A61N 1/3752 607/37 |
| 2005/0137665 A1 | 6/2005 | Cole |
| 2005/0171587 A1 | 8/2005 | Daglow et al. |
| 2005/0186829 A1 | 8/2005 | Balsells |
| 2005/0272280 A1 | 12/2005 | Osypka |
| 2006/0015163 A1 | 1/2006 | Brown |
| 2006/0025841 A1 | 2/2006 | McIntyre |
| 2006/0030918 A1 | 2/2006 | Chinn |
| 2006/0089681 A1* | 4/2006 | Tumlinson ........... A61N 1/3752 607/37 |
| 2006/0167522 A1 | 7/2006 | Malinowski |
| 2006/0224208 A1 | 10/2006 | Naviaux |
| 2006/0247697 A1 | 11/2006 | Sharma et al. |
| 2006/0247749 A1 | 11/2006 | Colvin |
| 2006/0259106 A1 | 11/2006 | Arnholt et al. |
| 2007/0042648 A1 | 2/2007 | Balsells |
| 2007/0142889 A1 | 6/2007 | Whitehurst et al. |
| 2007/0150036 A1 | 6/2007 | Anderson |
| 2007/0161294 A1 | 7/2007 | Brase et al. |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0139031 A1 | 6/2008 | Ries et al. |
| 2008/0177167 A1 | 7/2008 | Janzig et al. |
| 2008/0208277 A1 | 8/2008 | Janzig et al. |
| 2008/0208278 A1 | 8/2008 | Janzig et al. |
| 2008/0208279 A1 | 8/2008 | Janzig et al. |
| 2008/0215125 A1 | 9/2008 | Farah et al. |
| 2008/0255647 A1 | 10/2008 | Jensen et al. |
| 2008/0274651 A1 | 11/2008 | Boyd et al. |
| 2009/0054941 A1 | 2/2009 | Eggen et al. |
| 2009/0187222 A1 | 7/2009 | Barker |
| 2009/0204192 A1 | 8/2009 | Carlton et al. |
| 2009/0264943 A1 | 10/2009 | Barker |
| 2009/0276021 A1 | 11/2009 | Meadows et al. |
| 2009/0287191 A1 | 11/2009 | Ferren et al. |
| 2010/0029127 A1 | 2/2010 | Sjostedt |
| 2010/0030298 A1 | 2/2010 | Martens et al. |
| 2010/0036468 A1 | 2/2010 | Decre et al. |
| 2010/0057176 A1 | 3/2010 | Barker |
| 2010/0070012 A1 | 3/2010 | Chinn et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0004267 A1 | 1/2011 | Meadows |
| 2011/0005069 A1 | 1/2011 | Pianca |
| 2011/0022100 A1 | 1/2011 | Brase et al. |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0184480 A1 | 7/2011 | Kast et al. |
| 2011/0238129 A1 | 9/2011 | Moffitt et al. |
| 2011/0245903 A1 | 10/2011 | Schulte et al. |
| 2011/0270330 A1 | 11/2011 | Janzig et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0053646 A1 | 3/2012 | Brase et al. |
| 2012/0071937 A1 | 3/2012 | Sundaramurthy et al. |
| 2012/0071949 A1 | 3/2012 | Pianca et al. |
| 2012/0165911 A1 | 6/2012 | Pianca |
| 2012/0185019 A1 | 7/2012 | Schramm et al. |
| 2012/0197375 A1 | 8/2012 | Pianca et al. |
| 2012/0203302 A1 | 8/2012 | Moffitt et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0232603 A1 | 9/2012 | Sage |
| 2012/0253443 A1 | 10/2012 | Dilmaghanian et al. |
| 2012/0259386 A1 | 10/2012 | DeRohan et al. |
| 2012/0316615 A1 | 12/2012 | DiGiore et al. |
| 2013/0053864 A1 | 2/2013 | Geroy et al. |
| 2013/0098678 A1 | 4/2013 | Barker |
| 2013/0105071 A1 | 5/2013 | DiGiore et al. |
| 2013/0109254 A1 | 5/2013 | Klardie et al. |
| 2013/0116754 A1 | 5/2013 | Sharma et al. |
| 2013/0149031 A1 | 6/2013 | Changsrivong et al. |
| 2013/0197424 A1 | 8/2013 | Bedenbaugh |
| 2013/0197602 A1 | 8/2013 | Pianca et al. |
| 2013/0197603 A1 | 8/2013 | Eiger |
| 2013/0218154 A1 | 8/2013 | Carbunaru |
| 2013/0261684 A1 | 10/2013 | Howard |
| 2013/0288501 A1 | 10/2013 | Russell et al. |
| 2013/0304140 A1 | 11/2013 | Derohan et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0142671 A1 | 5/2014 | Moffitt et al. |
| 2014/0148885 A1 | 5/2014 | DeRohan et al. |
| 2014/0180375 A1 | 6/2014 | Pianca et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0025609 A1 | 1/2015 | Govea |
| 2015/0045864 A1 | 2/2015 | Howard |
| 2015/0066120 A1 | 3/2015 | Govea |
| 2015/0119965 A1 | 4/2015 | Govea |
| 2015/0151113 A1 | 6/2015 | Govea et al. |
| 2015/0209575 A1 | 7/2015 | Black |
| 2015/0360023 A1 | 12/2015 | Howard et al. |
| 2015/0374978 A1 | 12/2015 | Howard et al. |
| 2016/0059019 A1 | 3/2016 | Malinowski et al. |
| 2016/0129242 A1 | 5/2016 | Malinowski |
| 2016/0129265 A1 | 5/2016 | Malinowski |
| 2016/0158558 A1 | 6/2016 | Shanahan et al. |
| 2016/0206891 A1 | 7/2016 | Howard et al. |
| 2016/0228692 A1 | 8/2016 | Steinke et al. |
| 2016/0296745 A1* | 10/2016 | Govea ...................... A61N 1/36 |
| 2016/0375238 A1 | 12/2016 | Leven et al. |
| 2017/0072187 A1 | 3/2017 | Howard et al. |
| 2017/0143978 A1 | 5/2017 | Barker |
| 2017/0203104 A1 | 7/2017 | Nageri et al. |
| 2017/0361108 A1 | 12/2017 | Leven |
| 2018/0008832 A1 | 1/2018 | Leven |
| 2018/0028820 A1 | 2/2018 | Nageri |
| 2018/0093098 A1 | 4/2018 | Nageri et al. |
| 2018/0214687 A1 | 8/2018 | Nageri et al. |
| 2018/0243570 A1 | 8/2018 | Malinowski et al. |
| 2018/0289968 A1 | 10/2018 | Lopez |
| 2018/0369596 A1 | 12/2018 | Funderburk |
| 2019/0030345 A1 | 1/2019 | Funderburk |
| 2019/0083793 A1 | 3/2019 | Nageri |
| 2019/0083794 A1 | 3/2019 | Nageri |
| 2019/0103696 A1 | 4/2019 | Conger |

FOREIGN PATENT DOCUMENTS

| | | |
|---|---|---|
| EP | 0832667 B1 | 2/2004 |
| EP | 1181947 B1 | 1/2006 |

(56) References Cited

FOREIGN PATENT DOCUMENTS

| | | |
|---|---|---|
| EP | 1625875 | 2/2006 |
| EP | 2092952 A1 | 8/2009 |
| WO | 1997032628 A1 | 9/1997 |
| WO | 1999055411 A3 | 2/2000 |
| WO | 2000038574 A1 | 7/2000 |
| WO | 2001058520 A1 | 8/2001 |
| WO | 2002068042 A1 | 9/2002 |
| WO | 2004045707 A1 | 6/2004 |
| WO | 2008018067 A2 | 2/2008 |
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2009/148939 | 12/2009 |
| WO | 2013162775 A2 | 10/2013 |
| WO | 2014018092 A1 | 1/2014 |

* cited by examiner

LEAD ASSEMBLIES WITH ARRANGEMENTS TO CONFIRM ALIGNMENT BETWEEN TERMINALS AND CONTACTS

CROSS-REFERENCE TO RELATED APPLICATIONS

This application claims the benefit under 35 U.S.C. § 119(e) of U.S. Provisional Patent Application Ser. No. 62/451,513, filed Jan. 27, 2017, which is incorporated herein by reference.

FIELD

The present invention is directed to the area of implantable electrical stimulation systems and methods of making and using the systems. The present invention is also directed to implantable electrical stimulation systems having lead assemblies configured to confirm alignment between terminals on a lead or lead extension with contacts within a device or contact housing, as well as methods of making and using the lead assemblies and the electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a lead assembly that includes a lead or lead extension having terminals and a mechanical stop fixed to the lead or lead extension, the mechanical stop located distally to the plurality of terminals, the mechanical stop having an outer diameter. The lead assembly also includes a connector having a connector housing having a distal surface and a longitudinal axis, a connector block disposed within the connector housing, a port defined at the distal surface of the connector housing, a lumen extending from the port along the longitudinal axis of the connector housing and through the connector block, the lumen is configured for receiving a portion the lead or lead extension and has a lumen diameter within the connector block, and contacts disposed within the connector housing proximal to the connector block, where the contacts are configured to electrically couple to the terminals when the portion of the lead or lead extension is received within the lumen of the connector. The outer diameter of the mechanical stop is larger than the lumen diameter within the connector block to halt further insertion of the lead or lead extension into the connector housing.

In at least some embodiments, the lead or lead extension further includes a retention sleeve disposed distal to the plurality of terminals and proximal to the mechanical stop. In at least some embodiments, the mechanical stop and the retention sleeve are integrally formed.

In at least some embodiments, the mechanical stop is adhesively attached to the lead or lead extension. In at least some embodiments, the lead assembly is configured so that the mechanical stop, when in contact with the connector block, is entirely disposed within the connector housing. In at least some embodiments, the lead assembly is configured so that a portion of the mechanical stop extends outside of the connector housing when the mechanical stop is in contact with the connector block.

In at least some embodiments, the lead assembly is configured so that abutting the mechanical stop against the connector block aligns the terminals of the lead or lead extension with the contacts disposed in the connector housing. In at least some embodiments, the lead assembly further includes a fastener insertable into the connector block to securely fix the lead or lead extension to the connector block.

Another embodiment is a lead assembly that includes a lead or lead extension having terminals and a visually distinctive marking applied to the lead or lead extension, the marking located distally from the plurality of terminals. The lead assembly also includes a connector having a connector housing having a distal surface and a longitudinal axis, a connector block disposed within the connector housing, a port defined at the distal surface of the connector housing, a lumen extending from the port along the longitudinal axis of the connector housing and through the connector block, the lumen is configured for receiving a portion the lead or lead extension and has a lumen diameter within the connector block, and contacts disposed within the connector housing proximal to the connector block, where the contacts are configured to electrically couple to the terminals when the portion of the lead or lead extension is received within the lumen of the connector. The marking is configured and arranged such that, upon insertion of the lead or lead extension into the connector housing, longitudinal alignment of the terminals of the lead or lead extension with the contacts disposed in the connector housing is indicated by the marking being entirely masked by the connector housing.

In at least some embodiments, the lead or lead extension further includes a retention sleeve disposed distal to the plurality of terminals. In at least some embodiments, the marking is applied to the retention sleeve. In at least some embodiments, the marking has a color that visually contrasts with a color of the lead or lead extension and further visually contrasts with a color of the connector housing.

Yet another embodiment is a lead assembly that includes a lead or lead extension having terminals and a visually distinctive marking applied to the lead or lead extension, the marking located distally from the plurality of terminals, the marking having a proximal edge and a distal edge defining a longitudinal length of the marking The lead assembly also includes a connector having a connector housing having a distal surface and a longitudinal axis, a connector block disposed within the connector housing, a port defined at the distal surface of the connector housing, a lumen extending from the port along the longitudinal axis of the connector housing and through the connector block, the lumen is configured for receiving a portion the lead or lead extension and has a lumen diameter within the connector block, and contacts disposed within the connector housing proximal to the connector block, where the contacts are configured to electrically couple to the terminals when the portion of the lead or lead extension is received within the lumen of the connector. The marking is configured and arranged such that, upon insertion of the lead or lead extension into the connector housing, longitudinal alignment of the terminals of the lead or lead extension with the contacts disposed in the connector housing is indicated by alignment of a predetermined one of the distal edge or the proximal edge of the marking with the distal surface of the connector housing.

In at least some embodiments, the lead or lead extension further includes a retention sleeve disposed distal to the plurality of terminals and wherein the marking is applied to the retention sleeve. In at least some embodiments, the marking has a color that visually contrasts with a color of the lead or lead extension and further visually contrasts with a color of the connector housing.

A further embodiment is an electrical stimulating system that includes any of the lead assemblies described above and a control module coupleable to the lead assembly, the control module including a housing, and an electronic subassembly disposed in the housing. In at least some embodiments, the connector block is part of the control module. In at least some embodiments, the lead assembly includes the lead and a lead extension, wherein the connector housing is part of the lead extension.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads having biased ball-spring type contacts and connect assemblies, as well as methods of making and using the contacts, contact assemblies, and the electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,295,944; 6,391,985; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,831,742; 8,688,235; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated by reference in their entireties.

Examples of connectors, connector contacts and connector assemblies for electrical stimulation systems with leads are found in, for example, U.S. Pat. Nos. 8,849,396; 7,244,150; 8,600,507; 8,897,876; 8,682,439; U.S. Patent Applications Publication Nos. 2012/0053646; 2014/0148885; 2015/0209575; 2016/0059019; and U.S. Patent Provisional Patent Application Nos. 62/193,472; 62/216,594; 62/259,463; and 62/278,667, all of which are incorporated by reference in their entireties.

Figure 1:
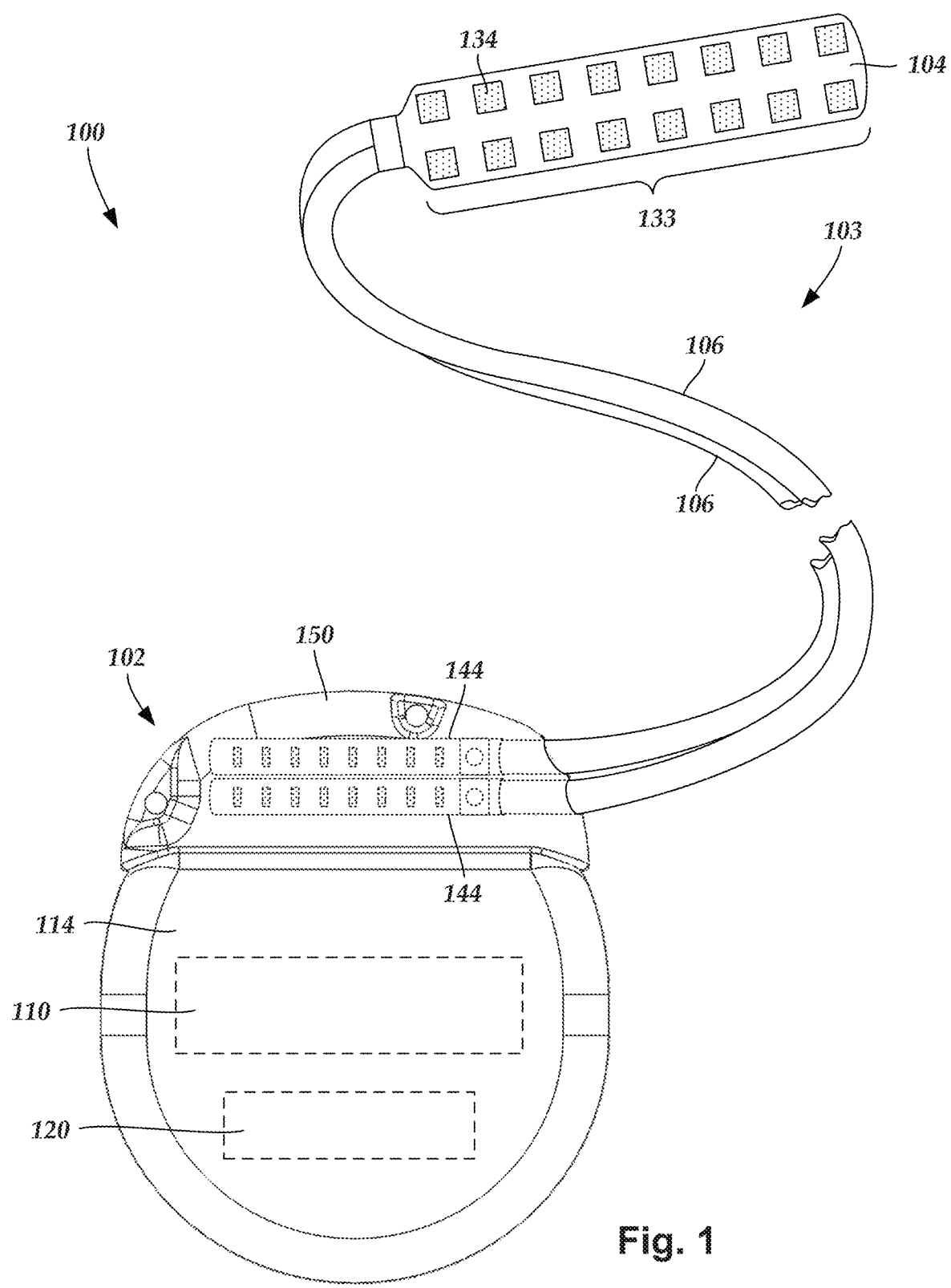
FIG. 1 is a schematic view of one embodiment of an electrical stimulation system that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102 and a lead 103. The lead 103 including a paddle body 104 and one or more lead bodies 106 coupling the control module 102 to the paddle body 104. The paddle body 104 and the one or more lead bodies 106 form the lead 103. The paddle body 104 typically includes a plurality of electrodes 134 that form an array of electrodes 133. The control module 102 typically includes an electronic subassembly 110 and an optional power source 120 disposed in a sealed housing 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contacts (e.g., 316 in FIG. 3A) disposed in the connector assembly 144 and terminals (e.g., 310 in FIG. 3A) on each of the one or more lead bodies 106. The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
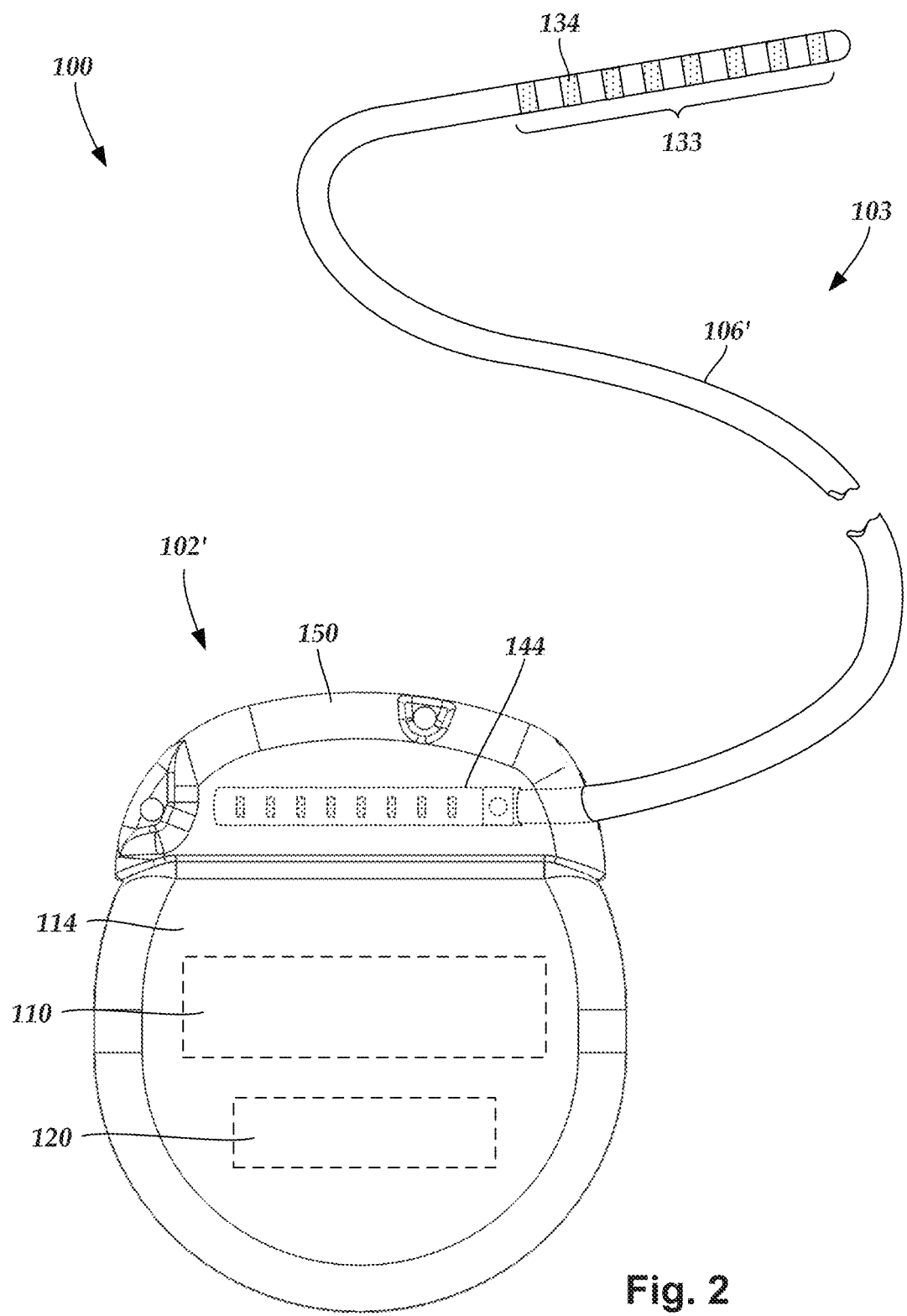
FIG. 2 is a schematic view of another embodiment of an electrical stimulation system that includes a percutaneous lead body coupled to a control module via a lead body, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of a lead body 106' forming a percutaneous lead 103, as illustrated in FIG. 2. The percutaneous lead may be isodiametric along the length of the lead body 106". The lead body 106' can be coupled with a control module 102' with a single connector assembly 144.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead 103 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A) are typically disposed at the proximal end of the one or more lead bodies 106 for connection to corresponding conductive contacts (e.g., 316 in FIG. 3A) in connector assemblies (e.g., 144 in FIG. 1) disposed on, for example, the control module 102 (or to other devices, such as conductive contacts on a lead extension, an operating room cable, a splitter, an adaptor, or the like).

Conductive wires (not shown) extend from the terminals (e.g., 310 in FIG. 3A) to the electrodes 134. Typically, one or more electrodes 134 are electrically coupled to a terminal (e.g., 310 in FIG. 3A). In some embodiments, each terminal (e.g., 310 in FIG. 3A) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

Figure 3A:
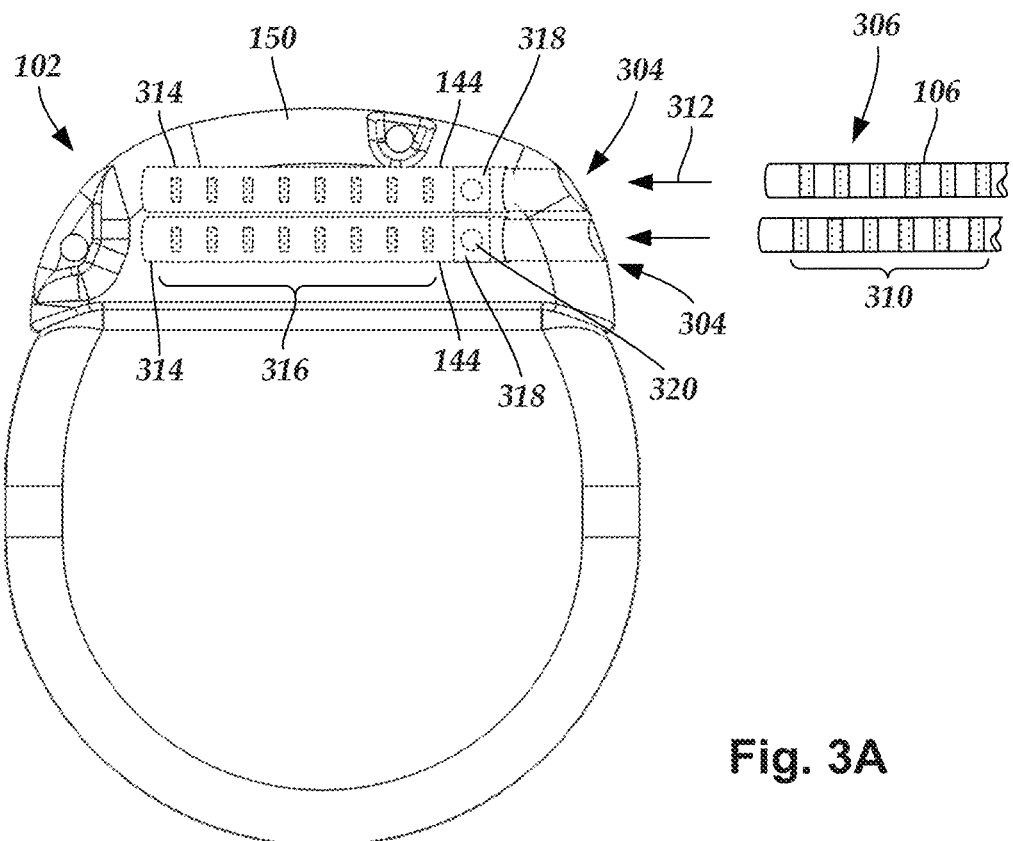
FIG. 3A is a schematic view of one embodiment of a plurality of connector assemblies disposed in the control module of FIG. 1, the connector assemblies configured and arranged to receive the proximal portions of the lead bodies of FIG. 1, according to the invention.
Figure 3B:
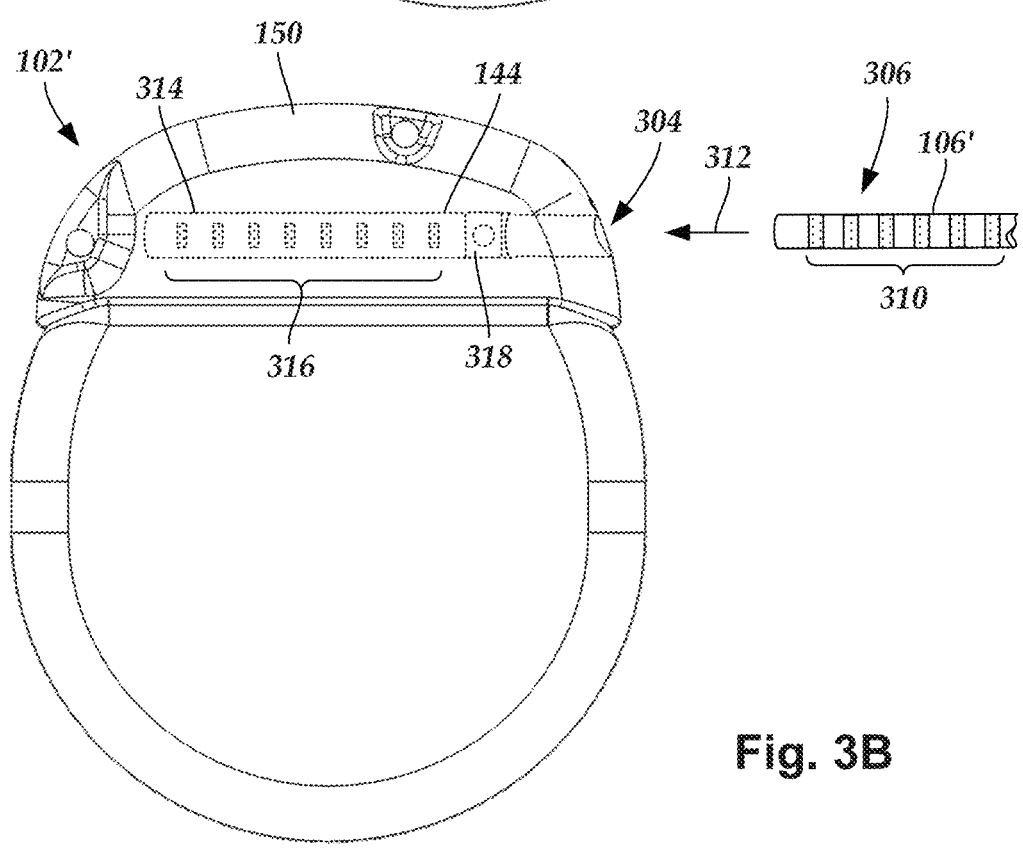
FIG. 3B is a schematic view of one embodiment of a connector assembly disposed in the control module of FIG. 2, the connector assembly configured and arranged to receive the proximal portion of one of the lead body of FIG. 2, according to the invention.

FIG. 3A is a schematic side view of one embodiment of a plurality of connector assemblies 144 disposed on the control module 102. In at least some embodiments, the control module 102 includes two connector assemblies 144. In at least some embodiments, the control module 102 includes four connector assemblies 144. In FIG. 3A, proximal ends 306 of the plurality of lead bodies 106 are shown configured and arranged for insertion to the control module 102. FIG. 3B is a schematic side view of one embodiment of a single connector assembly 144 disposed on the control module 102'. In FIG. 3B, the proximal end 306 of the single lead body 106' is shown configured and arranged for insertion to the control module 102'.

In FIGS. 3A and 3B, the one or more connector assemblies 144 are disposed in the header 150. In at least some embodiments, the header 150 defines one or more ports 304 into which the proximal end(s) 306 of the one or more lead bodies 106/106' with terminals 310 can be inserted, as shown by directional arrows 312, in order to gain access to the connector contacts disposed in the one or more connector assemblies 144.

The one or more connector assemblies 144 each include a connector housing 314 and a plurality of connector contacts 316 disposed therein. Typically, the connector housing 314 defines a port (not shown) that provides access to the plurality of connector contacts 316. In at least some embodiments, one or more of the connector assemblies 144 further includes a retaining element 318 configured and arranged to fasten the corresponding lead body 106/106' to the connector assembly 144 when the lead body 106/106' is inserted into the connector assembly 144 to prevent undesired detachment of the lead body 106/106' from the connector assembly 144. For example, the retaining element 318 may include an aperture 320 through which a fastener (e.g., a set screw, pin, or the like) may be inserted and secured against an inserted lead body 106/106'.

When the one or more lead bodies 106/106' are inserted into the one or more ports 304, the connector contacts 316 can be aligned with the terminals 310 disposed on the one or more lead bodies 106/106' to electrically couple the control module 102 to the electrodes (134 of FIG. 1) disposed at a distal end of the one or more lead bodies 106. Examples of connector assemblies in control modules are found in, for example, U.S. Pat. Nos. 7,244,150 and 8,224,450, which are incorporated by reference.

Figure 3C:
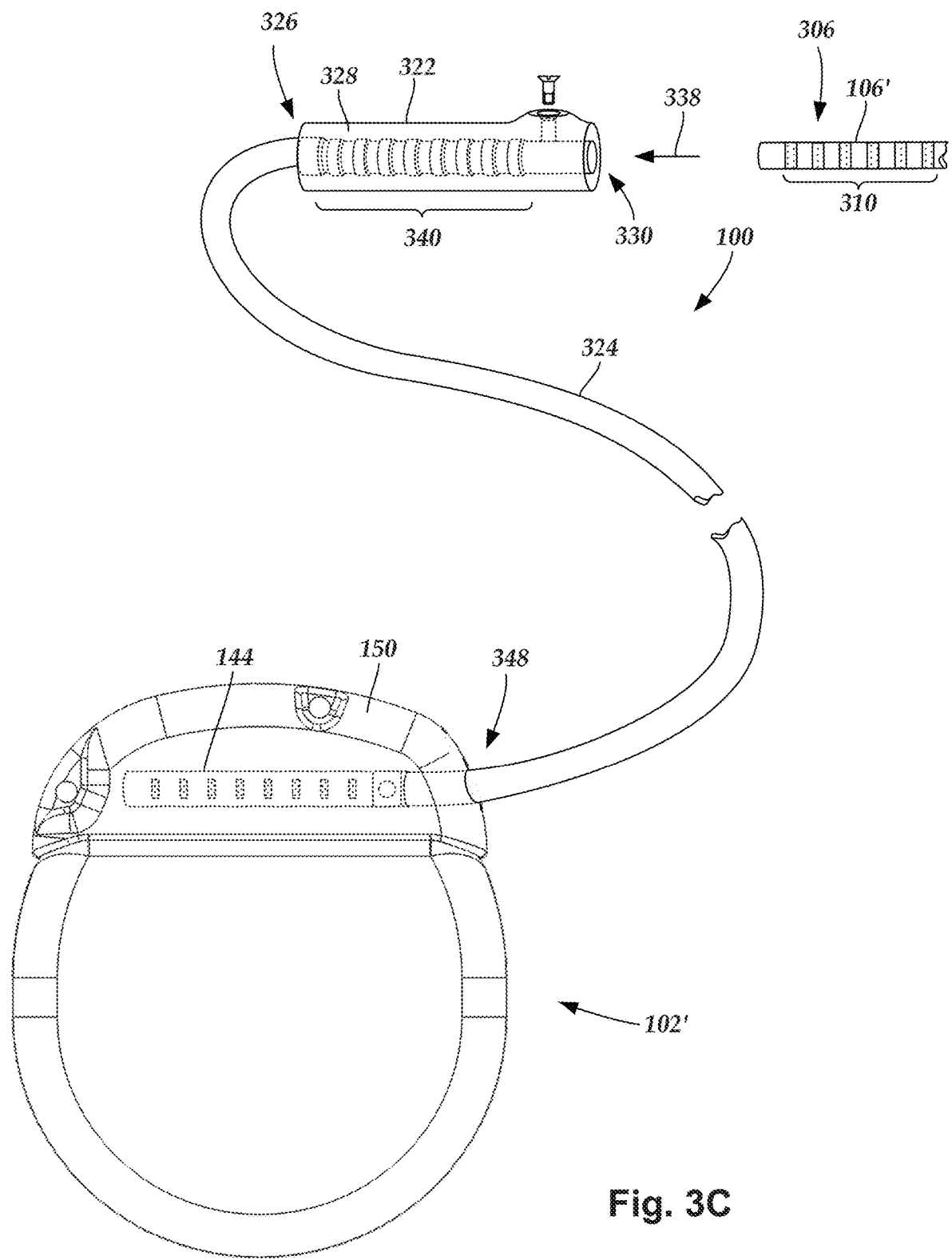
FIG. 3C is a schematic view of one embodiment of a proximal portion of the lead body of FIG. 2, a lead extension, and the control module of FIG. 2, the lead extension configured and arranged to couple the lead body to the control module, according to the invention.

In at least some embodiments, the electrical stimulation system includes one or more lead extensions. The one or more lead bodies 106/106' can be coupled to one or more lead extensions which, in turn, are coupled to the control module 102/102'. In FIG. 3C, a lead extension connector assembly 322 is disposed on a lead extension 324. The lead extension connector assembly 322 is shown disposed at a distal end 326 of the lead extension 324. The lead extension connector assembly 322 includes a contact housing 328. The contact housing 328 defines at least one port 330 into which a proximal end 306 of the lead body 106' with terminals 310 can be inserted, as shown by directional arrow 338. The lead extension connector assembly 322 also includes a plurality of connector contacts 340. When the lead body 106' is inserted into the port 330, the connector contacts 340 disposed in the contact housing 328 can be aligned with the terminals 310 on the lead body 106 to electrically couple the lead extension 324 to the electrodes (134 of FIG. 1) disposed at a distal end (not shown) of the lead body 106'.

The proximal end of a lead extension can be similarly configured and arranged as a proximal end of a lead body. The lead extension 324 may include a plurality of conductive wires (not shown) that electrically couple the connector contacts 340 to terminal on a proximal end 348 of the lead extension 324. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector assembly disposed in another lead extension. In other embodiments (as shown in FIG. 3C), the proximal end 348 of the lead extension 324 is configured and arranged for insertion into the connector assembly 144 disposed on the control module 102'.

It will be understood that the control modules 102/102' can receive either lead bodies 106/106' or lead extensions 324. It will also be understood that the electrical stimulation system 100 can include a plurality of lead extensions 224. For example, each of the lead bodies 106 shown in FIGS. 1 and 3A can, alternatively, be coupled to a different lead extension 224 which, in turn, are each coupled to different ports of a two-port control module, such as the control module 102 of FIGS. 1 and 3A.

In at least some conventional electrical stimulation systems, coupling a neuromodulation lead (or lead extension) to a device such as, but not limited to, a lead extension, a splitter, an adapter, a connector, an implantable pulse generator (IPG) header, is accomplished by longitudinally aligning the terminals of the lead (or lead extension) with the contacts of the device. Misalignment of the terminals vis-à-vis the contacts may occur because (1) the lead is not fully inserted into the device or (2) because the lead is pushed too far into the device. By way of example, pushing the lead too far into a connector housing may cause the housing to stretch, thus creating a misalignment between the terminals on the lead and the contacts within the connector housing.

To confirm proper alignment, a mechanical stop located distally from the terminals of the lead can be coupled to, or integrally formed with the lead. The mechanical stop includes an outside diameter larger than an inner diameter of the connector or connector block into which the lead is being inserted. This difference in diameters or interference can provide a hard stop to halt further insertion of the lead into the connector. Additionally or alternatively, proper alignment may be confirmed by using a visually distinctive marking or band applied on the lead and also located distally from the terminals of the lead. The marking or band would provide a visual indication and confirmation that the lead is inserted to the proper depth into the connector. Although the present description refers to a lead, it will be understood that the mechanical stop or visually distinctive marking can also be applied to a lead extension to facilitate alignment of the terminals of the lead extension with contacts in a connector. In addition, the connector described herein can be the connector on a lead extension, adapter, splitter, implantable pulse generator, or any other connector for a lead or lead extension in an electrical stimulation system.

Figure 4:
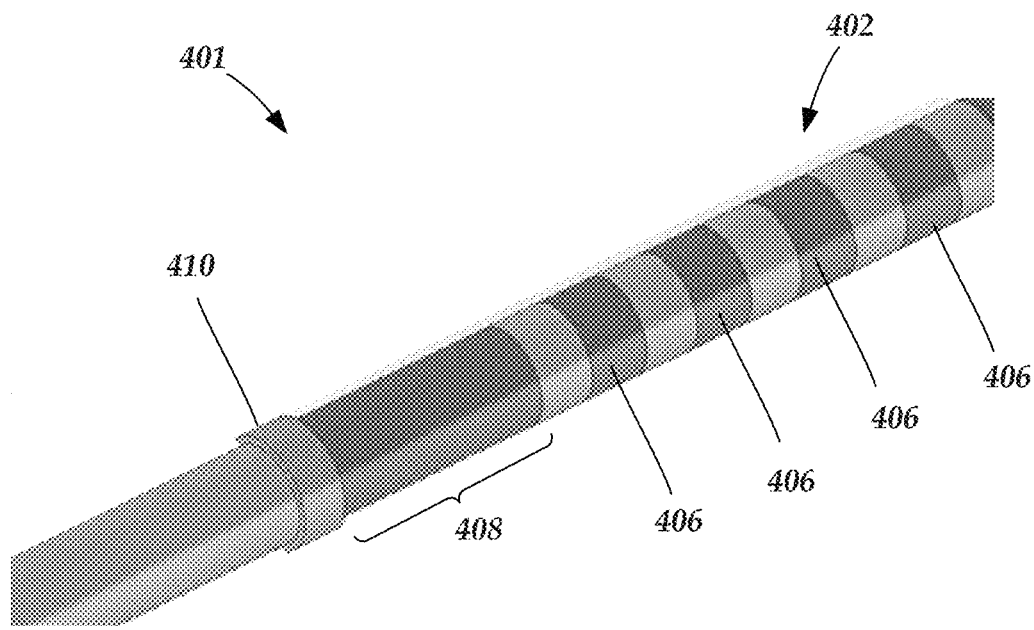
FIG. 4 is a schematic, perspective view of a lead or lead extension with a mechanical stop according to at least some embodiments of the present invention.

FIG. 4 shows a schematic, perspective view of a portion of a proximal end 402 of a lead or lead extension 401. A plurality of terminals 406 are arranged along the proximal end 402. The terminals 406 may take the form of terminals 310 in FIG. 3C. Optionally, a retention sleeve 408 is coupled to the lead or lead extension 401 and located distally from the terminals 406. Further, a mechanical stop 410 is coupled to the lead or lead extension 401 distally from the terminals 406. In at least some embodiments, the mechanical stop 410 is slid onto the lead or lead extension and mechanically coupled thereto (for example, bonded or adhered, press fit, shrink fit, or the like) adjacent or spaced-apart from the terminals 406. In at least some other embodiments, the mechanical stop 410 can be part of the retention sleeve 408 (e.g., integrally formed with) or the mechanical stop 410 can be an extension of the retention sleeve 408.

Figure 5:
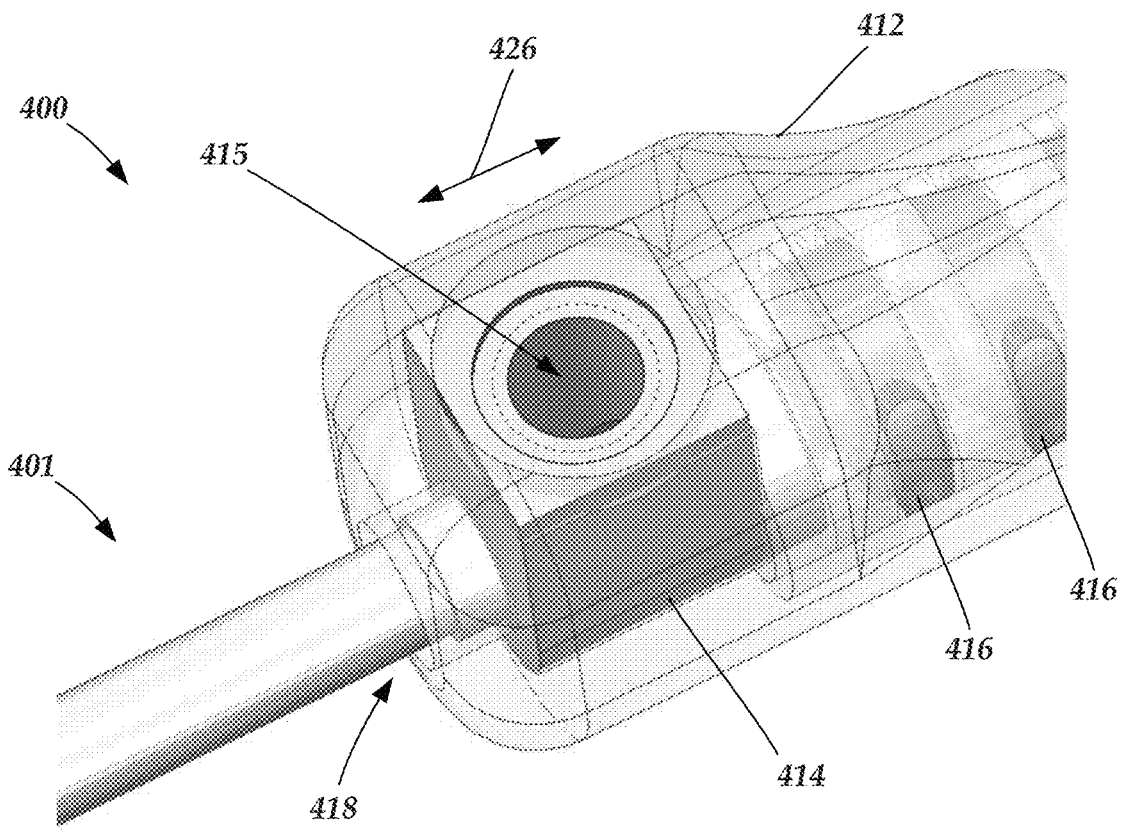
FIG. 5 is a schematic, perspective view of a lead assembly with a lead or lead extension having a mechanical stop inserted into a contact housing according to at least some embodiments of the present invention.

FIG. 5 shows a schematic, perspective view of a lead assembly 400 in which a lead or lead extension 401 is inserted into a connector housing 412 of a connector, which may optionally include a connector block 414 located distally to a plurality of contacts 416 disposed within the connector housing 412. By way of example, the connector housing 412 may be similar to the contact housing 328 in FIG. 3C. The connector housing 412 is made from a non-conductive, biocompatible material including, for example, silicone, polyurethane, and the like or combinations thereof. The contacts 416 may be disposed in, or separated by, the connector housing 412 or another non-conductive, biocompatible material such as, for example, silicone, polyurethane, polyetheretherketone ("PEEK"), epoxy, and the like or combinations thereof. The contacts 416 themselves can be formed using any conductive, biocompatible material. Examples of suitable materials include metals, alloys, conductive polymers, conductive carbon, and the like, as well as combinations thereof. In at least some embodiments, one or more of the contacts are formed from one or more of: platinum, platinum iridium, palladium, palladium rhodium, or titanium.

The connector block 414 can be made from a rigid or hard material and, at least in some embodiments, is threaded to receive a set screw (FIG. 3C), which can be used to secure the lead or lead extension 401 when the set screw is placed into a set screw aperture 415 to engage the retention sleeve 408 (FIG. 4) or the lead or lead extension 401. Other methods of fixing the lead or lead extension to the connector can also be used. The connector housing 412 defines at least one port 418 into which a portion of the lead or lead extension 401 can be inserted (as shown). The port 418 leads to a through channel 424 (FIG. 6) in the connector block 414. The channel 424 may be considered to be part of or a continuation of a lumen within the connector housing 412.

Figure 6:
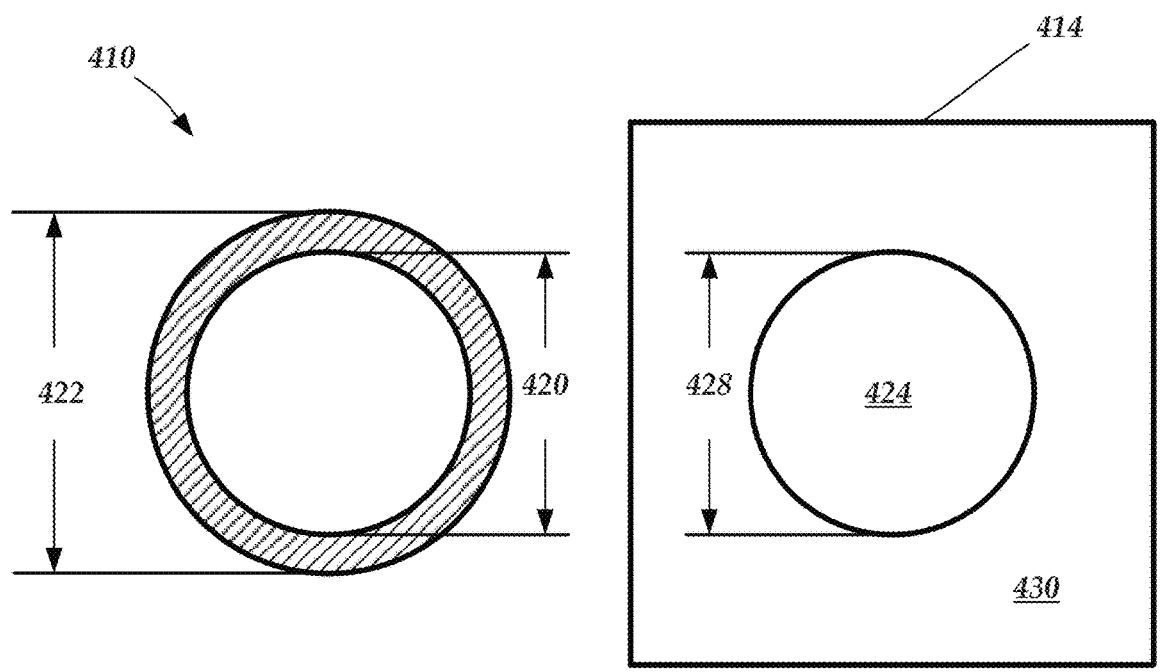
FIG. 6 is a schematic, cross-sectional view of the mechanical stop of FIG. 4 and a schematic, side-elevational view of a connector block with the contact housing of FIG. 5 according to at least some embodiments of the present invention.

FIG. 6 shows a cross-sectional view of the mechanical stop 410 and a side, elevational view of the connector block 414 as viewed from the port 418. In at least some embodiments, the mechanical stop 410 takes the form of a ring having an inner diameter 420 and an outer diameter 422. The connector block 414 includes the channel 424 that extends through the connector block 414 along an axial or longitudinal direction as indicated by arrow 426 (FIG. 5) of the lead or lead extension 401, which in turn coincides with an axial or longitudinal direction 426 (FIG. 5) of the connector housing 412. The channel 424 defines a channel diameter 428 (or lumen diameter), which is smaller than the outer diameter 422 of the mechanical stop 410. In at least some embodiments, the channel diameter 428 is at least slightly larger than the inner diameter 420 of the mechanical stop 410, but smaller than the outer diameter 422 of the mechanical stop 410. Accordingly, insertion of the lead or lead extension 401 into the connector block 414 is halted when the mechanical stop 410 physically contacts a distal surface 430 of the connector block 414 because the outer diameter 422 of the mechanical stop 410 is larger than the channel diameter 428 of the connector block 414.

Referring back to FIGS. 4 and 5, the mechanical stop 410, when in contact with a distal surface 430 (FIG. 6) of the connector block 414, can be disposed fully within the connector housing 412 between the port 418 of the contact housing and the distal surface 430 of the connector block 414. Alternatively, a portion of the mechanical stop 410 may extend outside of the connector housing 412 after the mechanical stop 410 has made physical contact with the distal surface 430 of connector block 414.

In at least some embodiments, a fastener (not shown) such as, but not limited to, a set screw, can be inserted into the connector block 414 when the mechanical stop 410 contacts the distal surface 430 of the connector block 414. The fastener securely fixes the lead or lead extension to the connector block 414 by pressing on the retention sleeve 408 or by pressing on the lead or lead extension 401. In at least some embodiments, a length of the retention sleeve 408 is equal to or greater than a distance between a proximal side of the connector block 414 and a distal side 430 of the connector block 414.

Figure 7:
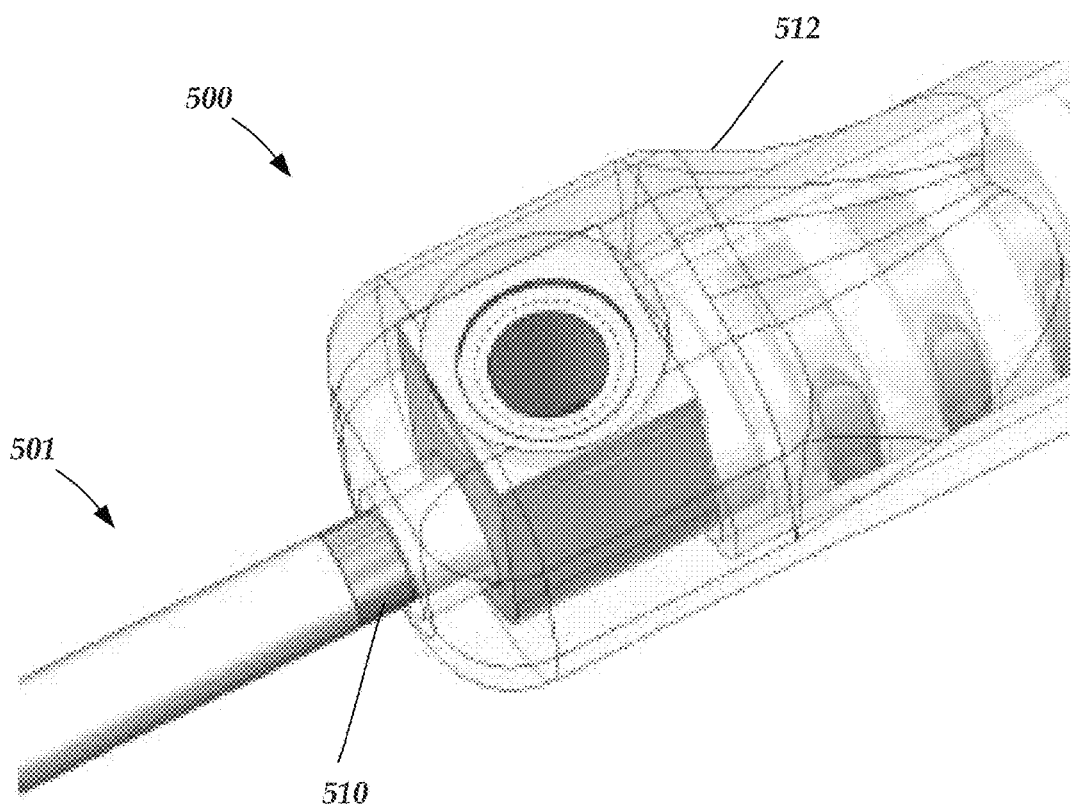
FIG. 7 is a schematic, perspective view of a lead assembly with a lead or lead extension having a visually distinctive marking being inserted into a contact housing according to at least some embodiments of the present invention.

FIG. 7 shows a schematic, perspective view of a lead assembly 500 in which a lead or lead extension 501 is inserted into a connector housing 512 of a connector. In the illustrated embodiment, a visually distinctive marking 510 (such as a band) may be utilized instead of a mechanical stop 410 (FIG. 4). In at least some embodiments, the marking 510 is applied to the lead or lead extension 501 distally from the terminals of the lead or lead extension 501. The location or position of the marking 510 relative to the distal end of the connector housing 512 provides a visible indication that the plurality of terminals of the lead or lead extension are aligned with the plurality of contacts disposed in the contact housing.

By way of example, the marking 510 may indicate alignment of the plurality of terminals and the plurality of contacts when a predetermined one of the leading or trailing edge of the marking 510 longitudinally aligns with the distal end of the connector housing 512. If the trailing edge of the marking 510 is aligned with the distal end of the connector housing 512 then the marking 510 would be fully covered by the connector housing 512. Thus, insertion of the lead or lead extension 501 would be halted and secured to the connector housing 512 once the marking 510 disappeared into the connector housing 512. In another embodiment, aligning the leading edge of the marking with the distal end of the connector housing 512 would indicate that the lead or lead extension has been inserted to a proper depth within the connector housing 512.

In at least some embodiments, the marking 510 may be an extension of or applied to the optional retention sleeve.

Preferably, the marking has a color that visibly contrasts with the color of the lead or lead extension 501 and further visibly contrasts with the color of the connector housing 512.

Figure 8:
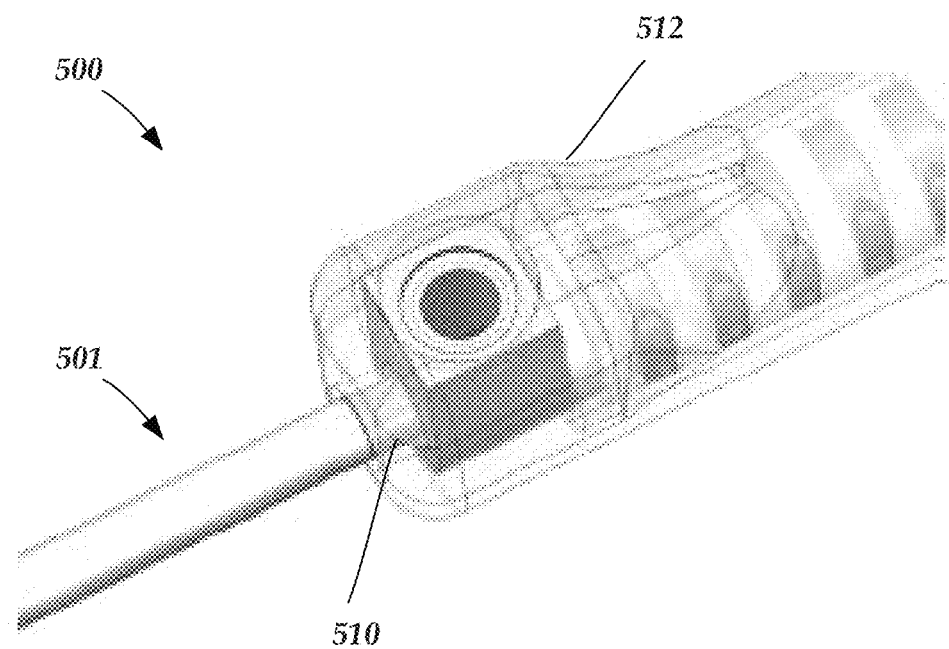
FIG. 8 is a schematic, perspective view of the lead assembly of FIG. 7 with the visually distinctive marking fully inserted into the contact housing.

FIG. 8 shows a schematic, perspective view of the lead assembly 500 in which the marking 510 has been inserted enough to be fully covered by the connector housing 512. In this embodiment, the terminals of the lead or lead extension 501 are longitudinally aligned with the contacts disposed within the connector housing 512.

Figure 9:
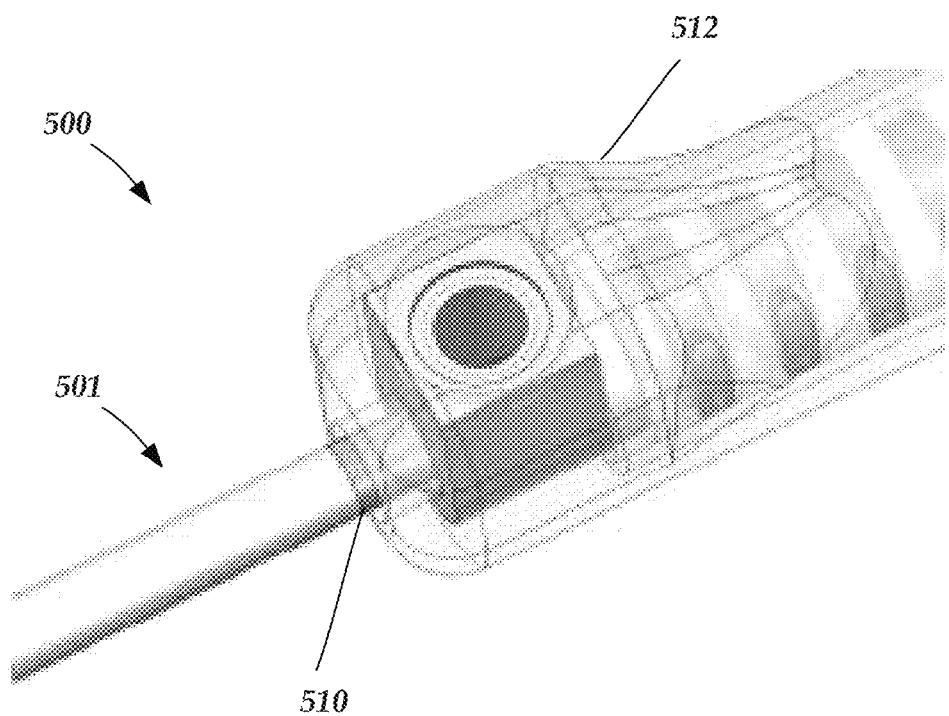
FIG. 9 is a schematic, perspective view of the lead assembly of FIG. 7 with the visually distinctive marking not yet fully inserted into the contact housing.

In contrast, FIG. 9 shows a small region of the marking 510 still exposed (i.e., not fully covered by the connector housing 512), which would indicate that the lead or lead extension 501 requires further insertion for proper alignment between the terminals and contacts can be confirmed.

Figure 10:
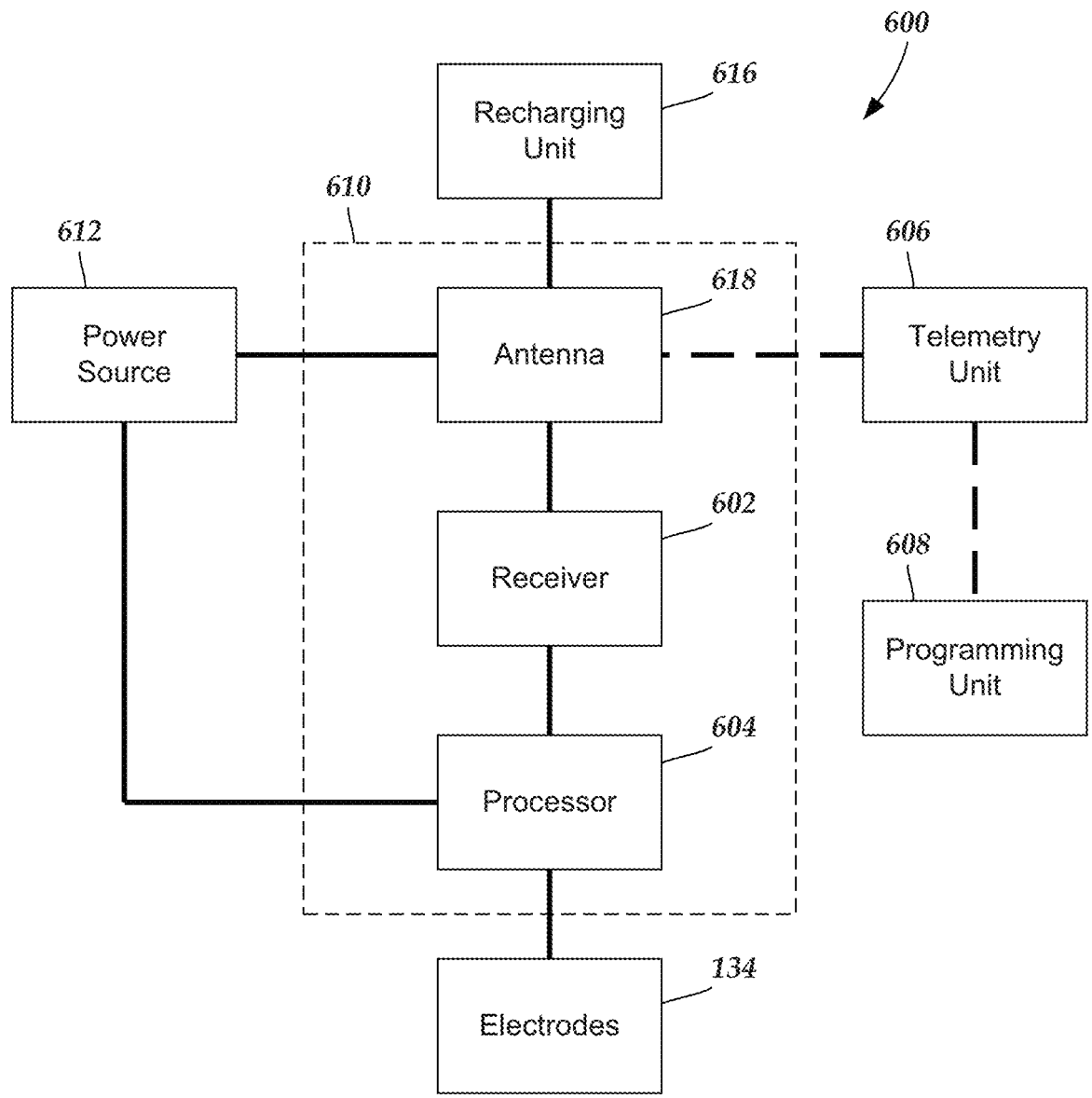
FIG. 10 is a schematic overview of one embodiment of components of a stimulation system, including an electronic subassembly disposed within a control module, according to the invention.

FIG. 10 is a schematic overview of one embodiment of components of an electrical stimulation system 600 including an electronic subassembly 610 disposed within a control module. It will be understood that the electrical stimulation system can include more, fewer, or different components and can have a variety of different configurations including those configurations disclosed in the stimulator references cited herein.

Some of the components (for example, a power source 612, an antenna 618, a receiver 602, and a processor 604) of the electrical stimulation system can be positioned on one or more circuit boards or similar carriers within a sealed housing of an implantable pulse generator, if desired. Any power source 612 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 618 or a secondary antenna. The external power source can be in a device that is mounted on the skin of the user or in a unit that is provided near the user on a permanent or periodic basis.

If the power source 612 is a rechargeable battery, the battery may be recharged using the optional antenna 618, if desired. Power can be provided to the battery for recharging by inductively coupling the battery through the antenna to a recharging unit 616 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 604 is generally included to control the timing and electrical characteristics of the electrical stimulation system. For example, the processor 604 can, if desired, control one or more of the timing, frequency, strength, duration, and waveform of the pulses. In addition, the processor 604 can select which electrodes can be used to provide stimulation, if desired. In some embodiments, the processor 604 selects which electrode(s) are cathodes and which electrode(s) are anodes. In some embodiments, the processor 604 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 608 that, for example, allows modification of pulse characteristics. In the illustrated embodiment, the processor 604 is coupled to a receiver 602 which, in turn, is coupled to the optional antenna 618. This allows the processor 604 to receive instructions from an external source to, for example, direct the pulse characteristics and the selection of electrodes, if desired.

In one embodiment, the antenna 618 is capable of receiving signals (e.g., RF signals) from an external telemetry unit 606 which is programmed by the programming unit 608. The programming unit 608 can be external to, or part of, the telemetry unit 606. The telemetry unit 606 can be a device that is worn on the skin of the user or can be carried by the user and can have a form similar to a pager, cellular phone, or remote control, if desired. As another alternative, the telemetry unit 606 may not be worn or carried by the user but may only be available at a home station or at a clinician's office. The programming unit 608 can be any unit that can provide information to the telemetry unit 606 for transmission to the electrical stimulation system 600. The programming unit 608 can be part of the telemetry unit 606 or can provide signals or information to the telemetry unit 606 via a wireless or wired connection. One example of a suitable programming unit is a computer operated by the user or clinician to send signals to the telemetry unit 606.

The signals sent to the processor 604 via the antenna 618 and the receiver 602 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 600 to cease operation, to start operation, to start charging the battery, or to stop charging the battery. In other embodiments, the stimulation system does not include the antenna 618 or receiver 602 and the processor 604 operates as programmed.

Optionally, the electrical stimulation system 600 may include a transmitter (not shown) coupled to the processor 604 and the antenna 618 for transmitting signals back to the telemetry unit 606 or another unit capable of receiving the signals. For example, the electrical stimulation system 600 may transmit signals indicating whether the electrical stimulation system 600 is operating properly or not or indicating when the battery needs to be charged or the level of charge remaining in the battery. The processor 604 may also be capable of transmitting information about the pulse characteristics so that a user or clinician can determine or verify the characteristics.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected is:

1. A lead assembly comprising:
    a lead or lead extension comprising a plurality of terminals and a visually distinctive marking applied to the lead or lead extension, the marking located distally from the plurality of terminals; and
    a connector comprising
        a connector housing having a distal surface and a longitudinal axis,
        a connector block disposed within the connector housing,
        a port defined at the distal surface of the connector housing,
        a lumen extending from the port along the longitudinal axis of the connector housing and through the connector block, the lumen is configured for receiving a portion the lead or lead extension and has a lumen diameter within the connector block, and
        a plurality of contacts disposed within the connector housing proximal to the connector block, wherein the contacts are configured to electrically couple to the terminals when the portion of the lead or lead extension is received within the lumen of the connector,
    wherein the marking is configured and arranged such that, upon insertion of the lead or lead extension into the connector housing, longitudinal alignment of the terminals of the lead or lead extension with the contacts disposed in the connector housing is indicated by the marking being entirely masked by the connector housing.

2. The lead assembly of claim 1, wherein the lead or lead extension further comprises a retention sleeve disposed distal to the plurality of terminals.

3. The lead assembly of claim 2, wherein the marking is applied to the retention sleeve.

4. The lead assembly of claim 1, wherein the marking has a color that visually contrasts with a color of the lead or lead extension and further visually contrasts with a color of the connector housing.

5. The lead assembly of claim 1, further comprising a fastener insertable into the connector block to securely fix the lead or lead extension to the connector block.

6. An electrical stimulating system comprising:
 the lead assembly of claim 1; and
 a control module coupleable to the lead assembly, the control module comprising
  a housing, and
  an electronic subassembly disposed in the housing.

7. The electrical stimulating system of claim 6, wherein the connector is part of the control module.

8. The electrical stimulating system of claim 6, wherein the lead assembly includes the lead and a lead extension, wherein the connector is part of the lead extension.

9. A lead assembly comprising:
 a lead or lead extension comprising a plurality of terminals and a visually distinctive marking applied to the lead or lead extension, the marking located distally from the plurality of terminals, the marking having a proximal edge and a distal edge defining a longitudinal length of the marking;
 a connector comprising
  a connector housing having a distal surface and a longitudinal axis,
  a connector block disposed within the connector housing,
  a port defined at the distal surface of the connector housing,
  a lumen extending from the port along the longitudinal axis of the connector housing and through the connector block, the lumen is configured for receiving a portion the lead or lead extension and has a lumen diameter within the connector block, and
  a plurality of contacts disposed within the connector housing proximal to the connector block, wherein the contacts are configured to electrically couple to the terminals when the portion of the lead or lead extension is received within the lumen of the connector,
 wherein the marking is configured and arranged such that, upon insertion of the lead or lead extension into the connector housing, longitudinal alignment of the terminals of the lead or lead extension with the contacts disposed in the connector housing is indicated by alignment of a predetermined one of the distal edge or the proximal edge of the marking with the distal surface of the connector housing.

10. The lead assembly of claim 9, the lead or lead extension further comprises a retention sleeve disposed distal to the plurality of terminals and wherein the marking is applied to the retention sleeve.

11. The lead assembly of claim 9, wherein the marking has a color that visually contrasts with a color of the lead or lead extension and further visually contrasts with a color of the connector housing.

12. An electrical stimulating system comprising:
 the lead assembly of claim 9; and
 a control module coupleable to the lead assembly, the control module comprising
  a housing, and
  an electronic subassembly disposed in the housing.

13. The electrical stimulating system of claim 12, wherein the connector is part of the control module.

14. The electrical stimulating system of claim 12, wherein the lead assembly includes the lead and a lead extension, wherein the connector is part of the lead extension.

\* \* \* \* \*